United States Patent
Gonon et al.

(10) Patent No.: US 7,056,315 B2
(45) Date of Patent: Jun. 6, 2006

(54) LIPOSUCTION APPARATUS WITH PRESSURIZED LIQUID SPRAY AND LIPOSUCTION METHOD USING THE APPARATUS

(75) Inventors: Bertrand Gonon, Ternay (FR); Ignacio Garrido, Paris (FR)

(73) Assignee: Eschmann Holdings Limited, Lancing (GB)

( * ) Notice: Subject to any disclaimer, the term of this patent is extended or adjusted under 35 U.S.C. 154(b) by 353 days.

(21) Appl. No.: 10/289,483

(22) Filed: Nov. 6, 2002

(65) Prior Publication Data
US 2003/0105422 A1    Jun. 5, 2003

(30) Foreign Application Priority Data
Nov. 7, 2001    (FR)    .................... 01 14394

(51) Int. Cl.
*A61M 1/00*    (2006.01)
*A61B 17/22*    (2006.01)
(52) U.S. Cl. .................... 604/542; 604/35; 604/43; 604/506; 604/93.01; 604/164.11
(58) Field of Classification Search .................. 604/27, 604/28, 35, 43, 506, 93.01, 164.11, 542, 30, 604/36, 44; 606/41, 42, 159, 166, 167
See application file for complete search history.

(56) References Cited

U.S. PATENT DOCUMENTS

| 4,419,093 | A | * | 12/1983 | Deaton ........................ 604/540 |
| 4,519,385 | A |   | 5/1985  | Atkinson et al. |
| 5,242,387 | A |   | 9/1993  | Loughlin |
| 5,817,050 | A |   | 10/1998 | Klein |
| 5,931,807 | A | * | 8/1999  | McClure et al. ............... 604/27 |
| 6,120,519 | A | * | 9/2000  | Weber et al. ................. 606/170 |
| 6,423,027 | B1 | * | 7/2002  | Gonon ........................ 604/27 |
| 6,960,182 | B1 | * | 11/2005 | Moutafis et al. .............. 604/43 |
| 2003/0167053 | A1 | * | 9/2003  | Taufig ........................ 604/542 |
| 2003/0220674 | A1 | * | 11/2003 | Anderson et al. ............. 607/96 |
| 2004/0019447 | A1 | * | 1/2004  | Shachar ...................... 702/115 |
| 2004/0158150 | A1 | * | 8/2004  | Rabiner et al. ............. 600/439 |

FOREIGN PATENT DOCUMENTS

| DE | 200 09 786 | 10/2000 |
| EP | 0315557 | 5/1989 |
| EP | 0331313 | 9/1989 |
| EP | 0509131 | 10/1992 |
| EP | 0701825 | 3/1996 |
| FR | 2622114 | 4/1989 |
| FR | 2691624 | 12/1993 |
| FR | 2700958 | 8/1994 |
| FR | 2744369 | 8/1997 |
| WO | 95/03740 | 2/1995 |

(Continued)

*Primary Examiner*—Tatyana Zalukaeva
*Assistant Examiner*—M G. Bogart
(74) *Attorney, Agent, or Firm*—Davis & Bujold, P.L.L.C.

(57) ABSTRACT

The liposuction apparatus (1) comprises in combination a tubular canula (3) having at its distal extremity (18) one or more suction orifices (24) and connected at its proximate extremity (19) to a suction source (14) in communication with these orifices, and a hand piece (2) delivering a spray of working liquid (4) under pressure. The hand piece delivers the spray of liquid under pressure using a conduit opening into an ejection orifice which, when the canula is attached to the hand piece, is located opposite an ejection orifice in the canula located at its distal extremity. A liposuction method using the apparatus is also taught. This invention is of interest to manufacturers and users of surgical equipment.

26 Claims, 3 Drawing Sheets

| | FOREIGN PATENT DOCUMENTS | |
|---|---|---|
| WO | 96/09007 | 3/1996 |
| WO | 98/40021 | 9/1998 |
| WO | 98/44966 | 10/1998 |
| WO | 98/44968 | 10/1998 |
| WO | 99/13783 | 3/1999 |
| WO | 99/22656 | 5/1999 |
| WO | 99/33665 | 7/1999 |
| WO | 99/44514 | 9/1999 |
| WO | 99/44515 | 9/1999 |
| WO | 99/44521 | 9/1999 |
| WO | 99/65408 | 12/1999 |
| WO | WO 99/65407 * | 12/1999 |
| WO | WO 00/56232 * | 9/2000 |
| WO | 01/91827 | 12/2001 |
| WO | WO 03/039629 A1 * | 5/2003 |

* cited by examiner

FIG.1

LIPOSUCTION APPARATUS WITH PRESSURIZED LIQUID SPRAY AND LIPOSUCTION METHOD USING THE APPARATUS

FIELD OF THE INVENTION

The present invention concerns a liposuction apparatus with a pressurized liquid spray as well as a liposuction method using the apparatus.

BACKGROUND OF THE INVENTION

Liposuction or lipoaspiration is a cosmetic surgery technique that has been in use for about twenty years and which is rapidly becoming the most widely practiced cosmetic surgery procedure in the world.

It consists of using suction to eliminate localized deposits of excessive subcutaneous fat in certain areas of the body, for example, the chest, the buttocks, the hips, or the thighs.

The conventional apparatus for this type of intervention comprises a hollow cylindrical cannula with one or more orifices near its distal extremity. This cannula is connected at the other end to a suction source, generally a vacuum pump, for the purpose of suctioning fat cells through the orifices and then evacuating them through the hollow interior portion of the cannula. A receptacle for recovering the suctioned fat is placed between the cannula and the suction source.

During the intervention, the surgeon first uses a syringe to inject a tumescent solution into several locations in the fatty area to be treated. This solution—generally a mixture of anesthetic products, vasoconstrictors and disaggregators with physiological serum—softens the fatty tissue and facilitates the process of dislocating it using evacuation.

After having waited long enough for the tumescent solution to infiltrate and act, the surgeon makes one or more incisions in the patient's skin at appropriate locations over the area to be treated to serve as points of entry for the cannula extremity.

The surgeon introduces the cannula below the skin through one of these incisions and suctions the fat by repeatedly moving the cannula back and forth longitudinally in the fatty area to be treated. Thus, the subcutaneous fat is mechanically dislocated by the movement of the cannula and then evacuated using suction.

After having removed all the adipose material accessible from this orifice by changing the direction of cannula action, the surgeon removes the cannula and reintroduces the cannula through another point of entry. He or she repeats the preceding operation using a crossing technique, also called tunneling.

When it becomes too difficult to move the cannula through the fatty tissue, further tumescent solution is reapplied. This injection must be followed by a waiting period in order for the solution to infiltrate properly, prolonging the time required for the surgery.

The surgeon proceeds in this way until enough fat has been removed to correct the areas the patient is dissatisfied with.

While this technique is generally satisfactory because of its simplicity and effectiveness, it requires considerable physical effort on the part of the surgeon to move the cannula back and forth. The intervention is very physically taxing for the surgeon who, despite the high demand, cannot perform multiple operations in one day.

Furthermore, during the procedure the surgeon may become so tired from the effort expended that he moves in a random, uncontrolled or even rough fashion, so the fat is not removed homogeneously. This causes the appearance of esthetically objectionable "waves" or rolls of fat at the surface of the treated area.

In addition, another difficulty encountered during a liposuction intervention is that the fat cells are sometimes difficult to detach from surrounding tissue, often forming clumps or nodules that block the cannula.

In this case the cannula must be removed, unblocked and reintroduced, thereby prolonging the intervention needlessly and causing additional trauma.

Another solution consists of intensifying suction in order to eliminate the fat plug. However, this requires very strong pressure, which can coincidentally harm surrounding tissue.

One current approach to eliminating the risk of plugging consists of using a larger diameter cannula. Obviously, this inflicts more trauma on the patient due to introduction of a larger cannula and causes significant scarring, requiring more time for reabsorption.

The result is an intervention that is challenging for the surgeon, needlessly long and often painful for the patient, in which it is impossible to completely control fatty tissue extraction, often resulting in an irregular, unesthetic epidermal surface over the treated area.

SUMMARY OF THE INVENTION

The goal of the invention is to overcome these disadvantages by proposing a liposuction apparatus that is comfortable to manipulate and far less fatiguing for the surgeon. In addition, the apparatus of the invention improves emulsification of fatty cells, thereby eliminating blocked cannulas, even when using a small diameter cannula.

The invention also teaches a liposuction method with more uniform fatty cell extraction, thereby producing a more esthetic result.

Numerous liposuction devices have been proposed by the prior art in the hope of improving the conditions of liposuction procedures and overcoming the previously cited disadvantages.

For example, liposuction devices with a cannula that is either partially or completely moved by means of an electric motor or compressed air have been proposed. Such devices have been described, for example, in the following patent applications: FR 2.744.369, WO 98/44966, WO 98/40021, EP 0.701.825, FR 2.622.114, and EP 0.315.557.

Using devices of this type, the liposuction intervention is far less fatiguing for the surgeon. Actually, since the motor induces back and forth movement by the cannula, the surgeon need only guide cannula displacement through the adipose tissue, exerting relatively limited effort. However, a certain degree of discomfort persists for the surgeon, as the cannula vibrations are transmitted to the surgeon's upper member.

Furthermore, these devices do not propose any solution to the problem of lysis of the cells of the fatty nodules and they do not reduce the length of the intervention, which proceeds in the conventional manner.

Additionally, because they are motorized, these devices are complex and relatively expensive. They require systematic and extremely meticulous maintenance after each intervention and incur a high risk of failure. It is even considered advisable to always have a sterile conventional liposuction apparatus available in case of failure.

Moreover, since their complex mechanisms constitute a veritable breeding ground for bacteria, sterilizing these devices is problematic and often ineffective. Therefore, the use of these devices is associated with a serious risk of contamination.

There is also another known category of liposuction devices based on different principles. The goal of these devices is to improve disaggregation and emulsification of fatty tissue in order to make is softer. This facilitates displacement of the cannula within the emulsified tissue, allowing the surgeon to exert less effort.

Therefore, ultrasonic devices are known in the art, for example, those described in application numbers FR 2.700.958, FR 2.691.624, WO 99/13783, WO 99/33665, WO 99/44514, WO 99/44515, EP 0.509.131, WO 95/03740, WO 96/09007 and EP 0.331.313; laser devices such as the one disclosed in application number WO 99/22656; or devices that use hyper-frequency electromagnetic energy such as those in application numbers WO 98/44968 and WO 99/44521.

All of these devices heat the fat locally, causing it to melt for improved elimination. Once the fat is melted, the cannula can be more easily activated.

Although they are promising, all these systems have proven misleading and have not been the subject of significant development due to their exorbitant cost and excessive failure rate. Actually, with all the systems based on heating the area to be treated there is considerable risk of burning the tissue and adjacent organs.

In addition, these systems actually provide only slight relief from the pain the intervention causes the surgeon and they do not resolve the problem of cannula blockage.

Moreover, the structures of these systems are so complex that resterilization of these systems cannot be guaranteed.

Despite the number and diversity of devices proposed in the market, most surgeons performing this type of intervention still use a conventional liposuction apparatus, notwithstanding all its disadvantages.

Therefore, there is a widespread need for an improved liposuction apparatus to overcome these obstacles, as well as a liposuction method using such an apparatus.

To resolve this technical problem, the liposuction apparatus of the invention uses one or more sprays of working liquid under pressure to dissociate, disaggregate and emulsify the fatty cells before proceeding to suctioning.

Advantageously, the tumescent solution may be mixed with the working liquid and may be injected under pressure into the core of the fatty tissue using the cannula. In this way, the tumescent solution is spread throughout a greater depth and impregnates a large quantity of adipose tissue. Thus, the tumescent solution is diffused much better than if it were injected using a syringe, where it remains in a very localized area, as with prior art devices. Clearly, this improves its effectiveness.

Due to improved diffusion and penetration of the tumescent solution, the complete disaggregation of the fatty tissue, and the tissue being mixed in solution with the working liquid, the surgeon needs to exert only a very slight effort to move the cannula back and forth and can guide the cannula without resorting to force.

Since the surgeon is clearly more comfortable, he or she can work with more precision and regularity, devoting his time to actual liposculputure. Due to improved sensitivity, the surgeon can finish the procedure with less risk of repeating the procedure.

Furthermore, using the apparatus of the invention, the evacuated fat is in solution with the working liquid and becomes much more fluid than with traditional devices. Suction is improved and instances of plugging are far more rare. This makes it possible to use smaller diameter cannulas, which reduce trauma to the patient and leave less conspicuous scars.

The liposuction apparatus according to the invention combines a hand piece delivering a spray of pressurized working liquid and a tubular cannula with a distal extremity and a proximate extremity, having near the distal extremity at least one suction orifice and being connected at its proximate extremity to a suction source communicating with this orifice.

The hand piece delivers the spray of pressurized liquid in a sterile manner using a conduit opening into an ejection orifice which, when the cannula is attached to the hand piece, is located opposite an ejection orifice in the cannula located near its distal extremity.

The sterility required for any surgical intervention is totally ensured with the liposuction device of the invention. Actually, the majority of the components are single-use components: the sterile pouch containing the working liquid, the hydraulic connections (conduits and connectors), as well as the hand piece. Only the cannula is reusable, with its perfectly smooth design ensuring complete effectiveness and guaranteeing sterility.

In contrast to prior art systems, the apparatus of the invention is very simple and requires only minimal maintenance, as most of the system is disposable.

The liposuction procedure, according to the invention, comprises the following steps:

making at least one incision in the patient's epidermis;

introducing the distal extremity of the cannula into this incision and injecting a predetermined volume of working liquid containing a tumescent solution by aiming a continuous or pulsating spray of highly pressurized liquid;

after waiting for the time required for the tumescent solution to act, activating suction; and moving the cannula back and forth while suctioning the fat that has been emulsified by the working liquid through the suction orifices in the cannula.

According to a variation of this procedure, it is also possible to activate a permanent pulsating spray of working liquid under pressure during the suction phase.

Among the numerous advantages of the invention, it should be mentioned that there is not only less blood loss during the procedure, but recuperation and post-operative care are significantly improved.

BRIEF DESCRIPTION OF THE DRAWINGS

Other characteristics and features of the invention will be apparent from the detailed description which follows, taken with reference to the attached drawings, in which.

DETAILED DESCRIPTION OF THE INVENTION

The liposuction apparatus according to the present invention will now be described in detail with reference to FIGS. 1 through 6. Equivalent elements shown in the different drawings will bear the same reference numerals.

Figure 1:
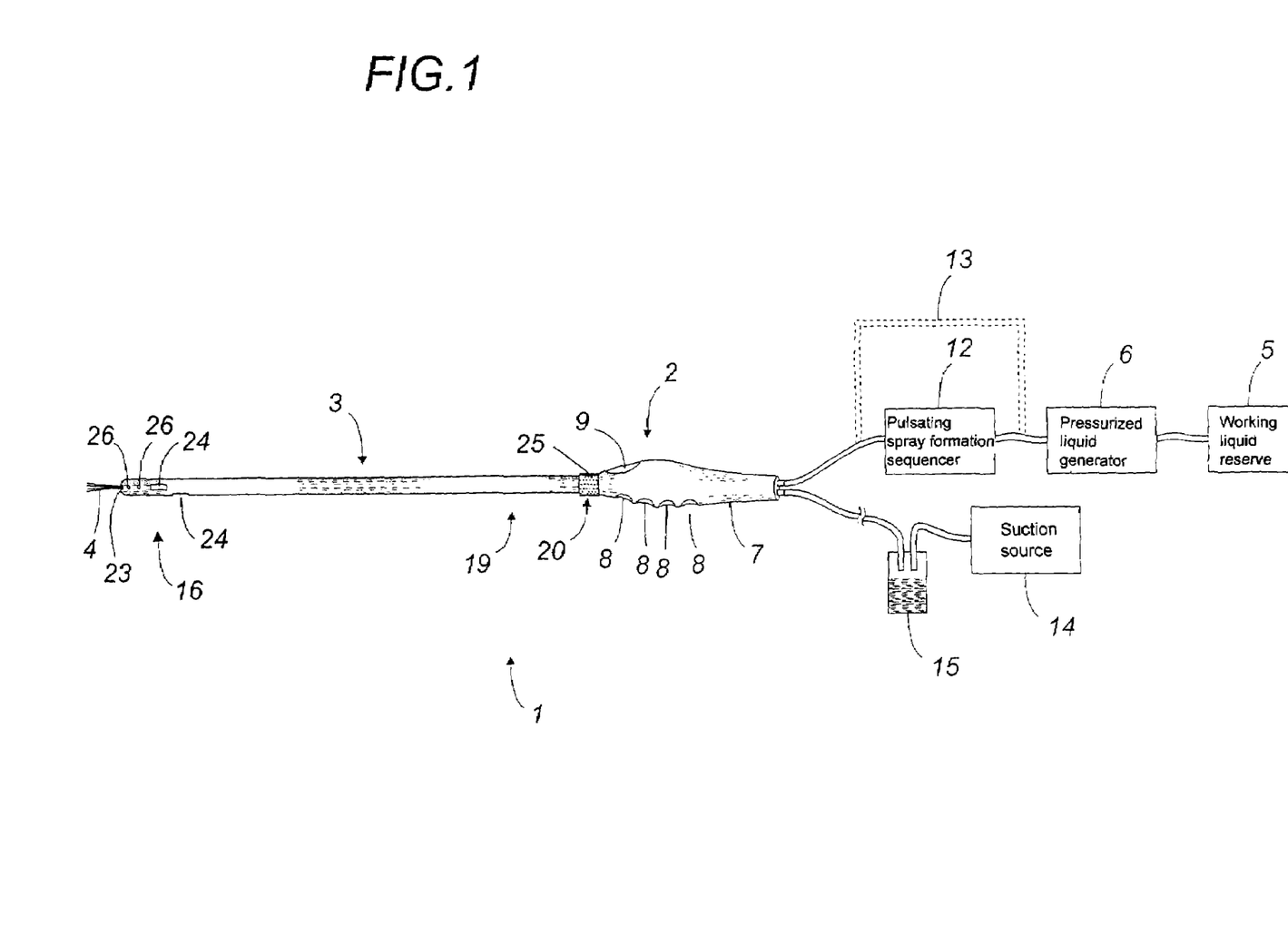
FIG. 1 is a general view of the liposuction apparatus according to the invention.
Figure 2:
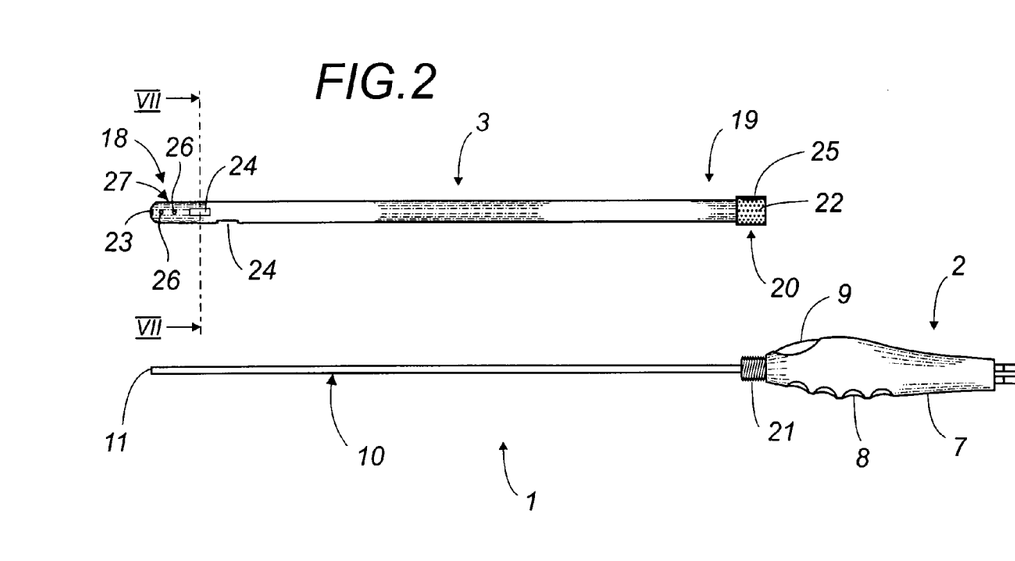
FIG. 2 is a side view of the hand piece and the liposuction cannula according to the invention when dismantled.

The liposuction apparatus 1 according to the invention comprises a hand piece 2 to which a liposuction cannula 3 may be attached.

Liposuction apparatus 1 allows one or more sprays 4 of sterile pressurized liquid to be aimed at the fatty tissue in order to disaggregate and emulsify the fatty tissue, allowing the fatty tissue to be suctioned far more easily.

For this purpose hand piece 2 is connected to a sterile reserve 5 of sterile working liquid which may be pressurized by a pressurized liquid generator 6.

The reserve is a disposable sterile container of sterile working liquid.

This reserve may consist, for example, of a flexible plastic pouch containing the sterile working liquid, enclosed in a sterile area that is pressurized by filling it with a neutral gas in order to compress the pouch and eject the pressurized liquid. The pressure of the liquid spray may be adjustable in order to adapt it to the situation. It is preferably about 20 bars for an ordinary liposuction procedure.

This pressure range allows the work to proceed with a diminished flow, thereby also reducing consumption of the liquid.

The enclosed area may also be heated to a temperature that is about equal to or slightly higher than 37° C. so the working liquid contacting the site of the procedure is approximately the same temperature as the patient's body.

The working liquid used is preferably sterile physiological serum. However, it is obvious that other sterile liquids may be used as the working liquid such as, for example, saline solution, glucose solution, Ringer-lactate, hydroxyethly-starch, or a mixture of these solutions.

Preferably the working liquid is composed of or comprises a tumescent solution, which may be dissolved in a physiological serum, for example. This tumescent solution is generally a mixture of products that produce different effects, such as a local anesthetic, a vasoconstrictor, and a disaggregating product.

For example, it is possible to use xylocaine, marcaine, nesacaine, novocain, diprivan, ketalar or lidocaine as the anesthetic agent.

Similarly, epinephrine, levorphanol, phenylephrine, athyl-adrianol or ephedrine may be used as vasoconstrictors in the tumescent solution to reduce blood flow at the site of the procedure.

The sterile working liquid, the temperature of which may have been previously regulated, moves into hand piece 2, allowing the surgeon performing the procedure to engage the spray of working liquid under pressure and direct it. The hand piece 2 comprises an ergonomic body 7 for ease of gripping and manipulation.

Hollow ergonomic depressions 8 may be provided below the hand piece to mark finger positions for the surgeon for more comfortable and precise gripping and manipulation. Similarly, on the upper portion of the hand piece, a depression 9 may be formed for the surgeon's thumb to rest.

Hand piece 2 may also comprise regulating elements such as, for example, pushbuttons (not shown) or simply orifices or sensitive zones, for example, tactile areas, for starting or stopping the spray of pressurized liquid and/or suction. These regulating elements may be located anywhere on the hand piece, for example, at or near finger-positioning depressions 8 and/or 9.

It is also possible for the apparatus according to the invention to be equipped with a control box that is independent of the hand piece, either manual or pedal operated.

Figure 3:
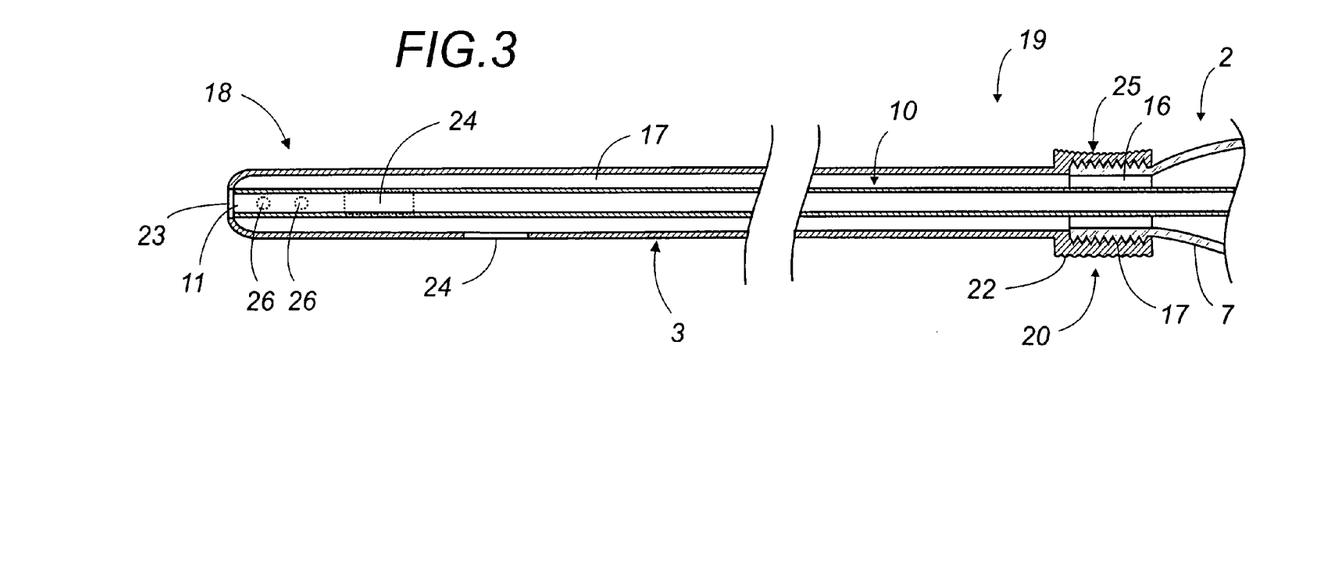
FIG. 3 is a cross-section of the extremity of the liposuction device according to the invention, with the cannula attached to the hand piece.

Hand piece 2 extends into conduit 10, terminating in small diameter ejection orifice 11 which moves the sterile pressurized working liquid and delivers it, but at a slow rate of speed, to the site of the intervention where it performs its job of disaggregating and emulsifying the fatty tissue.

By way of example, a 0.15 mm diameter results in a flow of 3 liters per hour, while a 0.22 mm diameter delivers 6 liters per hour when the pressure of the working liquid is between 10 and 20 bars.

The shape and small diameter of the outlet orifice allow the spray to remain fine and precise, which is desirable for numerous applications.

For improved effectiveness, liposuction apparatus 1 is preferably a pulsating spray sending the pressurized liquid by aiming series of impulses constituting elementary sprays of pressurized liquid, or one or more series of individual sprays. For this purpose liposuction apparatus 1 has a sequencer 12 to form a pulsated spray and control its parameters.

Nevertheless, without departing from the scope of the invention, liposuction apparatus 1 may also deliver a continuous spray of pressurized liquid. In this case sequencer 12 is superfluous. This simplified fluid circuit mode is shown diagrammatically in FIG. 1 by shunt 13 indicated with dotted lines.

In order to suction the fatty cells that have been emulsified by the spray of pressured liquid, liposuction apparatus 1 of the invention is connected to a suction source 14, for example, either to a vacuum pump or preferably to the general vacuum circuit of the clinic or hospital.

The suction source causes very high pressure, preferably approximately 1 bar, i.e., 1000 hectopascal.

A device (not shown) is provided for measuring the quantity of liquid injected, of product, and fatty tissue suctioned. Differential weight measurements are used to determine the quantity of dissolved fat and fatty tissue removed in order to decide the surgical procedure and achieve global balance.

A receptacle 15 for collecting the suctioned fat is interposed between hand piece 2 and suction source 14.

This may consist of a fat trap or a filtration unit for blocking fatty tissue.

The suction source terminates in suction conduit 16, concentric with conduit 10 and communicating with interior space 17 of cannula 3.

Cannula 3 may be removed from hand piece 2. For this reason, it may be snapped, screwed, slipped, or attached in some other way that allows removal for sterilization.

Cannula 3 has a distal extremity 18 and a proximate extremity 19 that facilitates attachment to hand piece 2, preferably being screwed to it.

For this purpose it comprises an essentially cylindrical ring with a threaded interior that can be screwed onto a threaded portion 21 formed in the extremity of the hand piece.

Ring 20 may further comprise on its external surface raised areas 22 to facilitate gripping and screwing.

The cannula 3 has, at is distal extremity, an ejection orifice 23 located opposite orifice 11 of conduit 10 when the cannula is positioned on hand piece 2, through which the spray 4 of pressurized working liquid exits.

It also has at its distal extremity 18 one or more fat-suctioning orifices 24 which, when the cannula is attached to the hand piece, communicate with suction source 14 via interior space 17 of the cannula, hand piece 2, and receptacle 15.

Without departing from the scope of the invention, these orifices may vary in number, shape, dimension, or position in comparison to those shown in the drawings, with all these characteristics being selected and optimized in terms of the patient, the part of the body to be treated, and the amount of fat to be removed.

Figure 4:
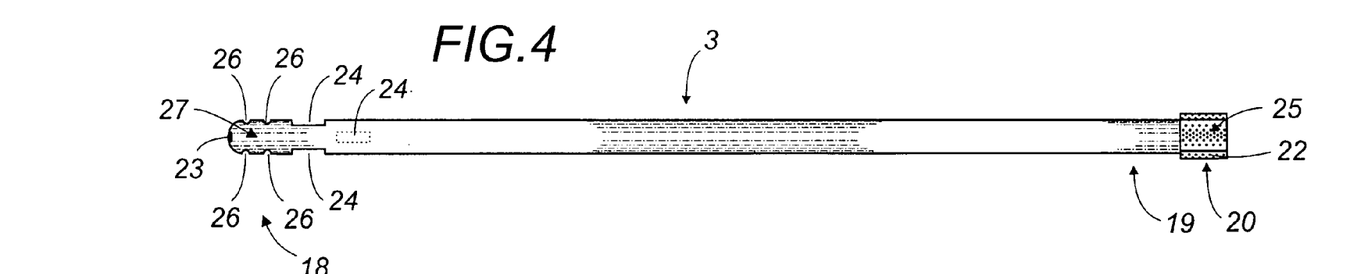
FIG. 4 is a top view of the liposuction cannula used in the invention.
Figures 5, 6:
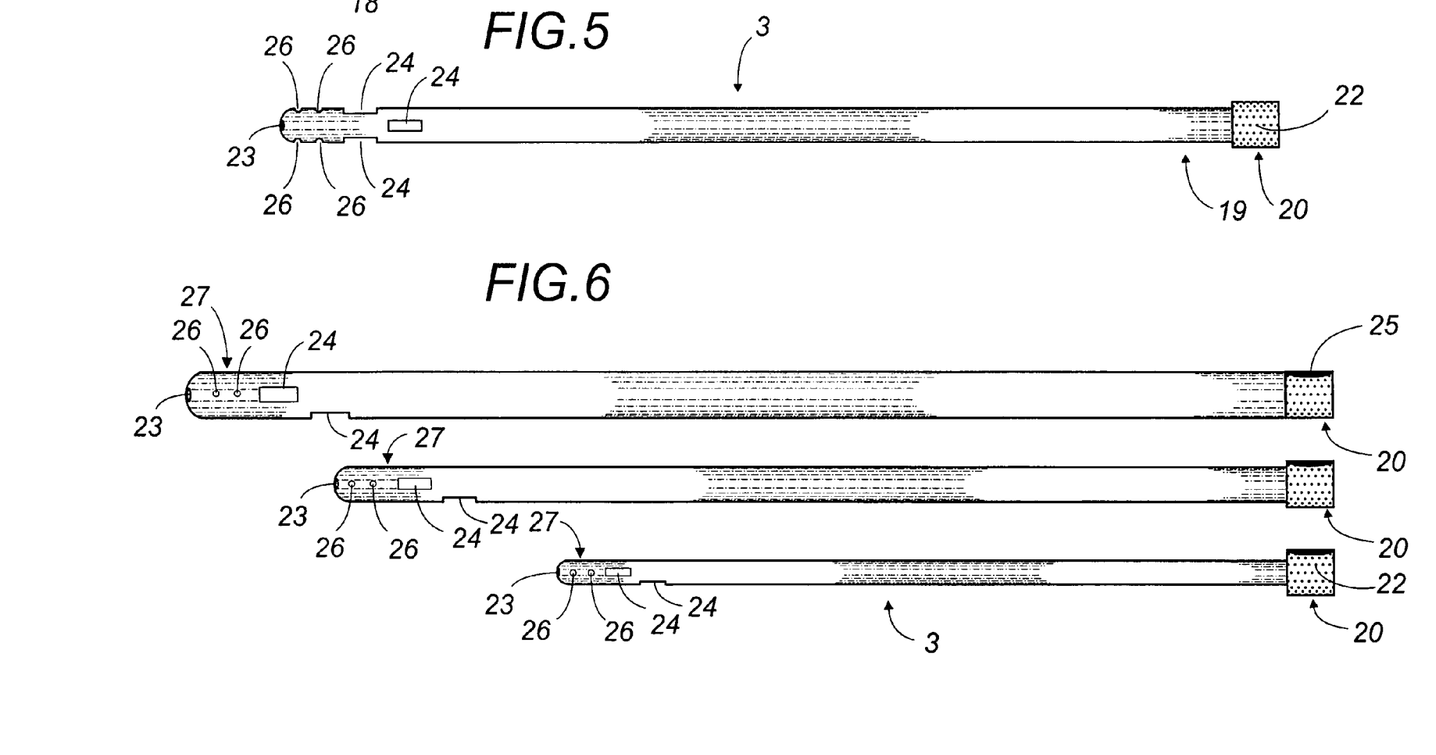
FIG. 5 is a bottom view of the liposuction cannula used in the invention.
FIG. 6 is a side view of different variations of the liposuction cannula used in the invention.

According to a preferred embodiment, these suction orifices 24 are three in number. The first two are arranged laterally at the same level on either side of the cannula, and the third at the lower portion of the cannula, offset from the two preceding orifices toward the proximate cannula extremity.

Preferably, at least one of these orifices is generally rectangular in shape, for example, about 1 cm wide by 0.3 cm high.

Figure 7:
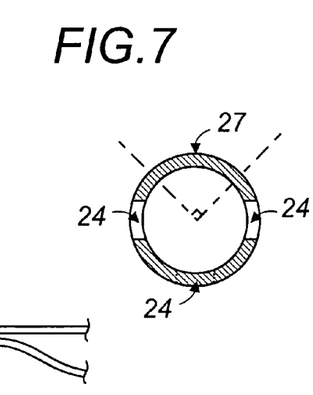
FIG. 7 is a cross sectional view of the liposuction cannula view when view along the sectional line VII—VII of FIG. 2.

However, in order to avoid damage to the patient's epidermis, the surgeon must completely avoid suctioning toward the skin. For this reason, the cannula must have an area 27 that is angled at about 90° and has no suction orifice. During the lipoaspiration procedure, this angular area must always be turned toward the skin.

Thus, the liposuction cannula according to the invention does not have any suction orifice at the upper portion.

To eliminate any risk of error, there is preferably an indicator 25 on the proximate extremity of cannula 3. This indicator shows the surgeon the portion of the cannula, without an orifice, that must be directed toward the skin. The presence of this indicator is very important because during the procedure, the surgeon can no longer see the position of the orifices, since the distal extremity of the cannula has been inserted beneath the skin of the patient. Indicator 25, located at the proximate extremity 19 of the cannula, for example on ring 20, always remains free and thus is always completely visible, allowing the surgeon to control proper positioning of the cannula.

This indicator 25 may be a simple marking, a raised area, a flat area, a depression designed to receive the tip of the surgeon's thumb as shown in the drawings, or any other means imaginable allowing the surgeon to easily locate the area that is free of orifices.

In addition, the distal extremity of liposuction cannula 3 may further comprise one or more orifices 26 of smaller dimension than fat-suctioning orifices 24.

These orifices 26, preferably four in number, accelerate fat suctioning using a venturi effect. In addition, if large suction orifices 24 become blocked, these small orifices 26 permit removal of the cannula.

Following the conventional practice for surgical material, the cannula has a distal extremity and orifices that are extremely smooth, that is, they have no rough projections, thus preventing them from tearing tissue and limiting trauma to the patient.

Depending upon the patient, the procedure to be performed, the part of the body to be treated, and the amount of fat to be removed, it may be preferable to use different models of liposuction cannulas.

Different variations of cannulas 3 may be used with the liposuction apparatus of the invention. Some examples of cannulas that can be used have been shown in FIG. 6.

These cannulas of different lengths and/or diameters all comprise a means for attaching them to the body of hand piece 2. For example, they are all equipped with an identical ring 20 which cooperates with threading 21 on the hand piece. Therefore, the liposuction apparatus of the invention offers the surgeon the choice of the optimal cannula for each procedure. The appropriate cannula is simply screwed onto the hand piece prior to the procedure.

The exterior diameter of cannula 3 preferably ranges from 3 to 7 mm. Its length may also vary, with the preferred length being about 30 cm.

According to a preferred embodiment, the liposuction cannula is made of stainless steel. Thus, it may be completely and effectively sterilized. Therefore, it can be reused after undergoing sterilization prior to each procedure.

The entire remainder of the fluid circuit is preferably made of plastic material, from the pouch holding the working liquid to the conduits and hydraulic connectors and the hand piece. All these elements are sterile and are single-use elements. They must be discarded after each procedure.

The sterility necessary for any surgical intervention is thus very easily achieved with the liposuction device according to the invention, which requires only extremely simple, limited maintenance.

A method for using the liposuction device described previously will now be explained.

Before beginning the procedure, the surgeon prepares the device and the products to be used. In particular, he checks the operation of the device which measures the amount of product injected and the amount of product and mass suctioned.

At the beginning of the intervention, the surgeon makes one or more incisions, depending upon the extent of the area to be treated.

He introduces the distal extremity of cannula 3 into the incision or incisions and injects a predetermined volume of working liquid, preferably composed of or containing a tumescent solution, by aiming a continuous or pulsating spray of liquid under high pressure without activating the suction.

He may successively orient the spray of working liquid in every direction abutting the fatty area to be treated that is accessible from the incision formed, in a sweeping motion.

He allows time for the injected product to act. When the surgeon does not feel any significant resistance to penetration of the cannula in the area to be treated, the liposuction work can begin. The surgeon can thus easily control the time necessary for the tumescent solution to act and emulsify the fatty cells and determine exactly the moment when suction can begin. The length of the procedure can be reduced in this way.

Next the surgeon activates the suction as well as a permanent pulsating spray of working liquid under pressure preferably ranging from 15 to 20 bars. He moves the cannula back and forth with no difficulty while suctioning the previously emulsified fat through the cannula orifices.

The surgeon moves over the entire accessible fatty area in this way. To limit the duration of the procedure, he begins suctioning in the same direction as the first spray of tumescent solution, then sweeps the area in the same way as before.

If there are multiple incisions, he then proceeds in the same way from another incision and so on, until the entire adipose area has been treated. To reduce waiting time the surgeon may begin, in this case, by injecting tumescent solution from each one of the incisions and then proceed to suctioning from the first incision while the solution infiltrates and acts on the fatty tissues adjacent the next incisions.

Through a simple control, it is also possible to proceed to simple suctioning without injecting working liquid.

The surgeon then simply suctions the fat by moving the cannula back and forth. When he encounters more resistance opposing this movement, he stops suctioning and releases another spray of pressurized liquid. He may then return to the work of suctioning.

Advantageously, during the entire duration of the procedure it is possible to control the volume injected as well as the volume suctioned.

This liposuction method, using a device which sprays liquid under pressure, results in more homogeneous removal of fat cells, and a more esthetic outcome.

The invention claimed is:

1. A liposuction apparatus having a tubular cannula, an injection source for injecting liquid, a suction source, and a hand piece, wherein:
   the hand piece (2) is sterile, disposable and delivers at least one jet (4) of working liquid under pressure;
   the tubular cannula (3) being removable from the hand piece (2) to facilitate resterilization and reuse thereof, the tubular cannula has a first distal extremity (18) with at least one suction orifice (24) and at least one ejection orifice (23) spaced from the at least one suction orifice (24) for ejecting sterile working liquid under pressure and a second proximate extremity (19) which facilitates releasable attachment of the tubular cannula (3) to the hand piece (2),
   a side surface of the tubular cannula (3) comprises an area (27), extending on an angular sector of about 90°, without any suction orifice;
   the suction source (14) communicates via a sterile disposable tube of the hand piece (2) with the suction orifice (24) at the first distal extremity (18);
   the injection source has a generator which generates pressurized sterile working liquid connected via a sterile disposable tube of the sterile disposable hand piece (2) with the ejection orifice (23) of the first distal extremity (18);
   a disposable reserve of the sterile working liquid supplies the generator with the working liquid;
   a device for measuring a quantity of the pressurized sterile working liquid injected and a quantity suctioned; and
   regulating means for regulating the temperature of the pressurized sterile working liquid so that the temperature of the pressurized sterile working liquid is approximately equal to that of the human body.

2. The liposuction apparatus according to claim 1, wherein the hand piece (2) delivers the at least one jet (4) of the sterile working liquid under pressure through a conduit (10) communicating with an ejection orifice (11) which, when the tubular cannula (3) is attached to the hand piece, is located so as to communicate with the ejection orifice (23) in the tubular cannula situated at the first distal extremity (18).

3. The liposuction apparatus according to claim 1, wherein the hand piece (2) is connected to a reserve (5) of working liquid which may be pressurized by the generator which is a pressurized liquid generator (6), and a receptacle (15), for recovering the suctioned fat, is interposed between the hand piece (2) and the suction source (14).

4. The liposuction apparatus according to claim 1, wherein the hand piece (2) delivers a single precise jet of pressurized working liquid.

5. The liposuction apparatus according to claim 1, wherein the pressure of the at least one jet ranges from 5 to 25 bars.

6. The liposuction apparatus according to claim 5, wherein the pressure of the at least one jet ranges from 10 to 20 bars.

7. The liposuction apparatus according to claim 6, wherein the pressure of the at least one jet is approximately 20 bars.

8. The liposuction apparatus according to claim 1, wherein a diameter of the ejection orifice (23) for ejecting the working liquid under pressure ranges from 0.1 to 2 mm.

9. The liposuction apparatus according claim 8, wherein the diameter of the ejection orifice (23) for ejecting the working liquid under pressure is one of 0.15 mm and 0.22 mm.

10. The liposuction apparatus according to claim 1, wherein the hand piece (2) delivers at least one pulsed jet of the pressurized working liquid.

11. The liposuction apparatus according to claim 10, wherein the liposuction apparatus comprises a sequencer (12) which forms the pulsed jet and controls parameters thereof.

12. The liposuction apparatus according to claim 1, wherein the working liquid comprises a tumescent solution.

13. The liposuction apparatus according to claim 1, wherein the hand piece (2) comprises an ergonomic body (7) equipped with hollow areas (8, 9) to mark locations for finger positioning.

14. The liposuction apparatus according to claim 1, wherein the liposuction apparatus further comprises control elements for engaging or stopping the at least one jet of pressurized liquid and the suction, located on one of the hand piece (2) or on a manual or pedal operated control box that is independent of the hand piece.

15. The liposuction apparatus according to claim 1, wherein the tubular cannula (3) is connected to the hand piece (2) by a threaded connection.

16. The liposuction apparatus according to claim 15, wherein the tubular cannula (3) comprises a generally cylindrical ring (20) with a threaded interior that can be screwed onto a threaded area (21) formed on the hand piece (2).

17. The liposuction apparatus according to claim 1, wherein the tubular cannula (3) has at least one suction orifice (24) that is generally rectangular in shape and which measures about 1 cm wide by 0.3 cm length.

18. The liposuction apparatus according to claim 1, wherein the distal extremity (18) of the tubular cannula (3) has at least one additional orifice (26) of a smaller size than the at least one suctioning orifice (24).

19. The liposuction apparatus according to claim 1, wherein a variety of different types of tubular cannulas (3) are connectable to the hand piece (2).

20. The liposuction apparatus according to claim 1, wherein the tubular cannula is made of stainless steel which may be sterilized, and a remainder of a fluid circuit is made of sterile single use plastic.

21. A liposuction apparatus having a tubular cannula, an injection source for injecting liquid, a suction source, and a hand piece, wherein the hand piece (2) is sterile, disposable and delivers at least one jet (4) of working liquid under pressure;
   the tubular cannula (3) being removable from the hand piece (2) to facilitate resterilization and reuse thereof, the tubular cannula has a first distal extremity (18) with at least one suction orifice (24) and at least one ejection orifice (23), spaced from the at least one suction orifice (24), for ejecting working liquid under pressure, and a second proximate extremity (19) which facilitates releasable attachment of the tubular cannula to the hand piece (2);

the suction source (14) communicates, via a sterile disposable tube of the hand piece (2), with the suction orifice (24) at the first distal extremity (18);

the injection source has a generator which generates pressurized sterile working liquid connected via a sterile disposable tube of the sterile disposable hand piece (2), with the ejection orifice (23) of the first distal extremity (18);

a disposable reserve of the sterile working liquid supplies the generator with the working liquid;

a device for measuring a quantity of the pressurized sterile working liquid injected and a quantity suctioned;

regulating means for regulating the temperature of the pressurized sterile working liquid so that the temperature of the pressurized sterile working liquid is equal or nearly equal to that of the human body; and the tubular cannula (3) has at least first, second and third suction orifices (24), the first and second suction orifices are located laterally at a same level on either side of the tubular cannula, and the third suction orifice is located at a lower portion of the tubular cannula, offset from the first and second suction orifices toward the proximate extremity (19) of the tubular cannula.

22. A liposuction method using a liposuction apparatus having a hand piece (2) which delivers at least one jet (4) of working liquid under pressure; a cannula (3) which is removable from the hand piece (2), via a proximate extremity (19) of the cannula, to facilitate resterilization and reuse thereof, the cannula has a distal extremity (18) with at least one suction orifice (24), for removing fatty tissue, and at least one ejection orifice (23), spaced from the at least one suction orifice (24), for ejecting working liquid under pressure; a suction source (14) communicating with the suction orifice (24); and an injection source generating a pressurized sterile working liquid and communicating with the ejection orifice (23); the method comprising the following steps:

making at least one incision in a patient's epidermis;

introducing the distal extremity (18) of the cannula (3) into the incision and injecting a predetermined volume of the working liquid containing a tumescent solution by one of a continuous and a pulsated jet of pressurized liquid;

activating suction after waiting for a time required for the tumescent solution to act; and moving the cannula (3) in a back and forth motion while suctioning fat that has been emulsified by the working liquid through the at least one suction orifice (24) in the cannula.

23. The liposuction method according to claim 22, wherein the method further comprises the step of activating a permanent pulsated jet of pressurized working liquid during the suction phase.

24. The liposuction method according to claim 22, further comprising step of pressurizing the working liquid in a range from 5 to 25 bars.

25. The liposuction method according to claim 22, further comprising the step of weighing quantities of pressurized liquid injected and of product suctioned and determining a quantity of one or more of tissue and fat extracted by subtraction.

26. The liposuction apparatus according to claim 1, wherein the tubular cannula (3) comprises an indicator (25) adjacent the proximate extremity (19) to indicate the area of the tubular cannula without any suction orifice.

* * * * *